United States Patent
Kluczynski et al.

(10) Patent No.: US 9,068,885 B2
(45) Date of Patent: Jun. 30, 2015

(54) METHOD AND APPARATUS FOR REMOTE DETECTION OF ALCOHOL VAPOR IN THE ATMOSPHERE

(71) Applicants: Pawel Kluczynski, Poznan (PL); Stefan Lundqvist, Askim (SE)

(72) Inventors: Pawel Kluczynski, Poznan (PL); Stefan Lundqvist, Askim (SE)

(73) Assignee: AIROPTIC SP. Z O.O., Poznan (PL)

( * ) Notice: Subject to any disclaimer, the term of this patent is extended or adjusted under 35 U.S.C. 154(b) by 75 days.

(21) Appl. No.: 13/901,260

(22) Filed: May 23, 2013

(65) Prior Publication Data
US 2013/0334419 A1  Dec. 19, 2013

(30) Foreign Application Priority Data
May 29, 2012  (PL) .......................................... 399354

(51) Int. Cl.
| | | |
|---|---|---|
| G01J 3/42 | (2006.01) | |
| G01N 21/35 | (2014.01) | |
| G01N 21/39 | (2006.01) | |
| G01N 33/98 | (2006.01) | |
| G01N 21/3504 | (2014.01) | |
| G01N 33/497 | (2006.01) | |

(52) U.S. Cl.
CPC ............... G01J 3/42 (2013.01); G01N 21/3504 (2013.01); G01N 33/4972 (2013.01)

(58) Field of Classification Search
CPC .... G01J 3/42; G01N 21/3504; G01N 33/4972
USPC ................ 250/339.12, 339.13, 343; 356/437; 422/84; 73/23.3
See application file for complete search history.

(56) References Cited

U.S. PATENT DOCUMENTS

| | | | |
|---|---|---|---|
| 5,349,187 A | 9/1994 | Azzazy et al. | |
| 5,907,407 A | 5/1999 | Atkinson et al. | |
| 7,095,501 B2 | 8/2006 | Lambert et al. | |
| 7,279,132 B2 | 10/2007 | Sultan et al. | |
| 7,292,153 B1 | 11/2007 | Ahmed | |
| 2003/0160173 A1 | 8/2003 | Ershov et al. | |
| 2004/0233433 A1* | 11/2004 | Uchida et al. ................. | 356/364 |
| 2010/0152976 A1* | 6/2010 | White et al. .................... | 701/48 |
| 2010/0188232 A1 | 7/2010 | Lambert et al. | |
| 2012/0050743 A1* | 3/2012 | Yanai et al. ................... | 356/437 |

FOREIGN PATENT DOCUMENTS

JP   A-2000-230900   8/2000

OTHER PUBLICATIONS

English-language Abstract of Polish Patent Application No. 389627; Published Nov. 20, 2009 in the name of Zygmunt et al.

(Continued)

Primary Examiner — Mark R Gaworecki
(74) Attorney, Agent, or Firm — Oliff PLC

(57) ABSTRACT

A light beam generated by a light source having a wavelength corresponding to the ethanol absorption spectrum, preferably in the wavelength range of 3.28-3.52 μm or in one or more wavelength ranges 6.49-7.46 μm, 7.74-8.33 μm, 8.84-10.10 μm, 10.7-12.00 μm, is sent through a measuring space containing a sample of exhaled breath, and then the intensity of the light beam passing through the measuring space is measured. Based on the spectral analysis of the dependence of the light intensity to the alcohol concentration, the concentration of ethanol vapor is determined and the information about the level of the ethanol content is provided to a suitable display or device.

26 Claims, 7 Drawing Sheets

(56) References Cited

OTHER PUBLICATIONS

Figure 1A:
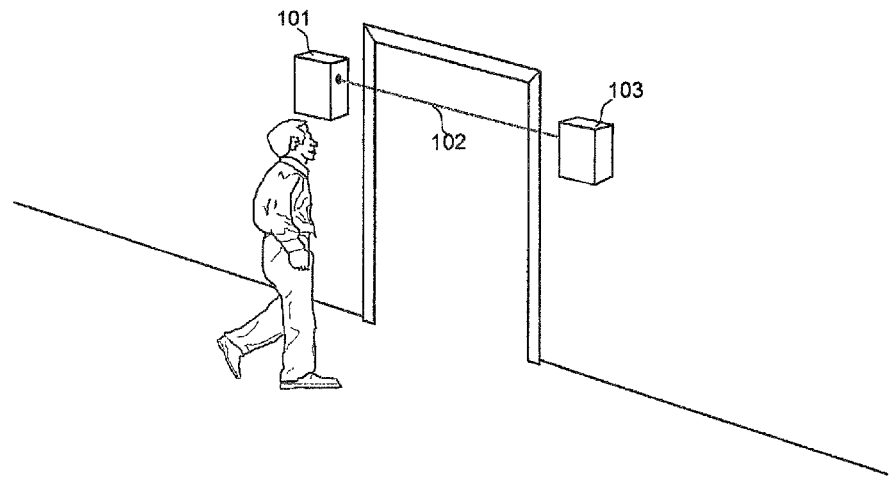

Hok et al., "Breath Analyzer for Alcolocks and Screening Devices," *IEEE Sensors Journal*, vol. 10, No. 1, pp. 10-15, Jan. 2010.

Beitel et al., "Probability of arrest while driving under the influence of alcohol," *Injury Prevention*, vol. 6, No. 2, pp. 158-161, 2000.

Alobaidi et al., "A helium-neon laser infrared analyser for alcohol vapour in the breath," *Journal of Physics E: Scientific Instruments*, vol. 8, pp. 30-32, 1975.

Azzazy et al., "Remote sensor to detect alcohol impaired drivers," *IEEE—Laser and Electro-Optics Society Annual Meeting*, vol. 2, pp. 320-321, 1995.

Nadezhdinskii et al., "Application of near-IR diode lasers for measurement of ethanol vapor," *Spectrochimica Acta Part A*, vol. 55, pp. 2049-2055, 1999.

Berezin et al., "Trace complex-molecule detection using near-IR diode lasers," *Applied Physics B*, vol. 75, pp. 203-214, 2002.

Schuetz et al., "A mid-IR DIAL System Using Interband Cascade Laser Diodes," *Proceedings of OSA/CLEO*, Paper JThD88, 2007.

Mitsubayashi et al., "Bioelectronic sniffers for ethanol and acetaldehyde in breath air after drinking," *Biosensors and Bioelectronics*, vol. 20, pp. 1573-1579, 2005.

Kamat et al., "Measurement of acetaldehyde in exhaled breath using a laser absorption spectrometer," *Applied Optics*, vol. 46, No. 19, pp. 3969-3975, Jul. 1, 2007.

Naehle et al., "Continuous-wave operation of type-1 quantum well DFB laser diodes emitting in 3.4 μm wavelength range around room temperature," *Electronics Letters*, vol. 47, No. 1, pp. 46-47, Jan. 6, 2011.

Bewley et al., "Ridge-width dependence of midinfrared interband cascade laser characteristics," *Optical Engineering*, vol. 49, No. 11, pp. 111116-1-111116-5, Nov. 2010.

Jennings, D.E., "Absolute line strengths in $v_4$, $^{12}CH_4$: a dual-beam diode laser spectrometer with sweep integration," *Applied Optics*, vol. 19, No. 16, pp. 2695-2700, Aug. 15, 1980.

\* cited by examiner

Spectrum of ethanol and water vapor together with the optical transmission of a typical car window Spectrum of ethanol and carbon dioxide together with the optical transmission of a typical car window Optical transmission in the 3,326 to 3,587 micron region, ethanol concentration 1 ppm Optical transmission in the 6,512 to 11,936 micron region, ethanol concentration 1 ppm

METHOD AND APPARATUS FOR REMOTE DETECTION OF ALCOHOL VAPOR IN THE ATMOSPHERE

This invention relates to a method and an apparatus for remote detection of alcohol vapor in the atmosphere, particularly useful for the determination of alcohol vapor in the air exhaled by a human in an area where it is forbidden to be under the influence of alcohol or entering such an area, The method and apparatus is also useful for detection of alcohol in exhaled breath while driving a vehicle. The invention also provides a device for remote sensing of alcohol vapor in the atmosphere.

Already in 1975 Alobadi et al. utilized a HeNe laser operating at 3.39 μm to detect alcohol vapor in exhaled breath. There is a broad ethanol absorption feature in the wavelength range 3.28 μm to 3.51 μm which can be interrogated by a 3.39 μm HeNe laser. However, the selectivity at this wavelength is poor due to the presence of similar absorption bands from other organic molecules. The system showed a minimum detectable concentration of 3 ppm. The HeNe laser is not tunable but its use in gas sensing relies on the fortunate coincidence between the laser emission line and an absorption line in the measured gas. The most notably coincidence is that between the HeNe laser 3.39 μm line and the lines in the $v_3$ band of methane which therefore will give a strong absorption signal at this wavelength. Methane can be expected to be present in small amounts in a vehicle compartment since it is generated by car engines. Therefore the 3.39 μm wavelength is not suitable for detection of ethanol in this environment since it is not specific for ethanol and the risk of interferences from other gases, most notably methane.

A similar system based on differential spectroscopy incorporating a HeNe laser at 3.49 μm was proposed in the patent application PL389627. Since the measurement is based on a difference between two signals taken at two fixed frequencies, one overlapping with the ethanol absorption band and the other outside the ethanol absorption band, the system is also very sensitive to cross interferences from other molecules present in the compartment and the atmosphere outside the vehicle. Moreover the ethanol absorption at 3.49 μm is only ⅓ of the maximum peak (proposed in this report) so that the detection limit of the system will not be sufficient to detect the small alcohol concentration levels of ethanol in the compartment required for efficient operation. The authors of the invention do not specify the detection limit reached by their system, the experiment was performed by evaporating 10 g of rectified alcohol in a car compartment. Assuming the compartment volume of 4 m3 this equals to approximately 1300 ppm of ethanol vapor, which is a very high value, not relevant to the alcohol levels generated by a drunk driver in a real life.

A system for remote detection of ethanol in vehicles was also proposed in the Japanese patent application JP 2000-230900 (A), "Alcohol detector in vehicle". The application was later withdrawn. The system utilizes two diode lasers, one with a wavelength on-absorption and one with a wavelength off-absorption. The inventors propose to operate the lasers in a pulsed mode so as to leave a time lag between the wavelengths which would make it possible to use one detector and time multiplexing to receive both channels. The pulse width is below 60 ns. No additional modulation was applied to the lasers. The alcohol detection is proposed to be performed by a discrimination of the pulse height and the criteria for the presence of alcohol would be decided by a set of logical gates. This signal processing will not be adequate to detect the ethanol concentrations in a vehicle occupied by a driver on the limit of legal alcohol consumption. Moreover, the wavelengths that have been chosen for detection of ethanol vapor, 2.75 μm on-absorption and 2.70 μm or 2.80 μm off-absorption respectively, will not allow to reach sufficient sensitivity and selectivity that is required for a practical sensor. The 2.75 μm lies on the edge of the 2.7 μmethanol band, where the absorbance is low, almost 20 times lower than the absorbance of the absorption peak at 3.345 μm proposed in this invention report. Thus the sensitivity of the instrument will not be sufficient to detect the low ethanol concentrations corresponding to the legal limit in most of the countries (53 ppm), a problem further amalgamated by the choice of signal processing. However, the main problem of the proposed solution is that absorption by water vapor and carbon dioxide, both present in ambient atmosphere, is very high in this wavelength region. Even in moderate climate conditions (1% water absolute vapor level and 380 ppm carbon dioxide level), the laser power will be completely absorbed over the distance required for the laser beam to reach the vehicle. The transmission change caused by absorption of ethanol in a 1.8 meter wide car compartment at 2.75 μm will be only 0.0001%! Differentiation of such a small transmission change form a vast and varying background using the proposed signal processing will be impossible.

A similar differential measurement has been published by M. Schuetz et. al. "A mid-IR DIAL system using interband cascade laser diodes", Proceedings of OSA/CLEO 2007 JThD88 paper). The authors used two types of lasers ICL (Interband Cascade Laser) at the wavelengths 3.38 μm and 3.54 μm. The proposed wavelengths in combination with the measuring method do not provide sufficient sensitivity and selectivity of measurement. In laboratory conditions, a detection limit of 40 ppm was obtained, which is nearly 100 times too high for such a system to be used in practice.

The described technique in (M. Azzazy et. al. "Remote sensor to detect alcohol impaired drivers," IEEE-Laser and Electro-Optics Society Annual Meeting, vol. 2, pp. 320-321, 1995) uses for the first time Tunable Diode Laser Spectroscopy (TDLS), with wavelength modulation spectroscopy (WMS) to detect alcohol. The system utilized the narrow Q-branch of ethanol near 1.392 μm. Other bands are rejected by the authors since they are subject to strong interferences from other gases or that they requires cryogenically cooled lasers. The system was a breadboard laboratory system using an absorption cell of 1 meter to simulate a typical car width. There is no indication of the minimum detectable concentration achieved with the LAA. Moreover, no provision was made to simultaneously measure a tracer gas from the exhaled breath such as $CO_2$ or $H_2O$ making it impossible to quantitatively relate the measured level of alcohol to the drivers blood alcohol level.

The same authors in U.S. Pat. No. 5,349,187 reveal a laser system for non-intrusive screening of drunk drivers. The described device uses the propagated light of a laser with a modulated wavelength, a detector and a signal analyzer based on spectroscopic detection of alcohol vapor, wherein the system components are located on opposite sides of the vehicle. The preferred embodiment utilizes a bench-top external cavity laser at the wavelength of 1.5 μm or a cryogenically cooled lead salt diode laser at a wavelength of 3.39 μm, where according to the authors the alcohol absorption lines are present. Ethanol has no absorption lines in the 1.5 μm region, there is also no isolated absorption peak at 3.39 μm just a continuous absorption spectra. As in the case of the above mentioned applications many other gases present in the atmosphere or in the cabin of the vehicle (such as methane, methanol, propane, and propylene), have similar broad absorption features in this region and it is not possible only using the absorption at 3.39 µm to avoid interference from other hydrocarbons. Moreover, the broad absorption continuum will not produce any signal at all utilizing WMS and that is why it is not possible that the disclosed invention will produce any measurable signal from ethanol. The reasons are incorrect wavelength assignments and absorption features not compatible with WMS.

The patent application No. US2003160173 reveals a system for the remote detection of ethanol vapor where a tunable laser propagating light wave with a wavelength of 1.392 µm is used. After passing through the measuring space, the ray is reflected by a system of mirrors and falls on the detector. A measuring method based on the detection of alcohol vapor at a wavelength of 1.392 µm does not give a sufficient measuring sensitivity and selectivity, not only because of low absorption of the alcohol vapor at that wavelength, but also because of the presence of strong interference by the signal caused by water vapor, which absorbs strongly at this wavelength. The application does not provide information on the obtained measuring accuracy and limit of detection. The same group, however, has published two articles (A. Nadezhdinskii et. al. Spectrochimica Acta A, vol. 55, pp. 2049-2055, 1999, and Berezin et. al. Applied Physics B, Volume 75 p. 203-214, 2002) where the detection limit was 350 ppm in the laboratory. It is almost a thousand times more than the limit of detection required for authoritative measurement of alcohol (i.e. 53 ppm, which also will be diluted in the cabin by car ventilation, etc.).

U.S. Pat. No. 5,907,407 reveals an extractive onboard assembly using the method of ILS (Intra cavity Laser Spectroscopy) which increases the sensitivity. Three different wavelengths are proposed to measure the alcohol vapor, namely: 1.39 µm, 2.74 µm, 3.39 µm, where the best measurement of the vapor concentration was obtained at a wavelength of 3.39 µm. As in the other cases described above, none of the wavelength are suitable for sufficiently accurate and selective measurement of alcohol vapor due to interference from other gases present in the atmosphere or in the exhaled air, particularly water vapor and methane. In addition, this device does not allow remote measurement of alcohol vapor as it needs to be mounted in the passenger compartment.

U.S. Pat. No. 7,292,153 reveals a system for remote detection of alcohol in the blood of the driver, indirectly by measuring the acetaldehyde vapor in the breath. Ethanol must be oxidized before it is removed from the human body. The main part of the ethanol is oxidized in the liver to acetaldehyde by the enzyme alcohol dehydrogenase. Acetaldehyde is therefore present in the exhaled breath after drinking alcohol. Generally, the level of acetaldehyde vapor in exhaled air is 10-100 times lower than in the vapor of ethanol itself after drinking alcohol. Because of individual differences in alcohol conversion efficiency between people, the concentration of acetaldehyde in the breath varies a lot between individuals (K V Mitsubayashi et. al., Biosensors and Bioelectronics, Vol 20, pp. 1573-1579, 2005). There is no simple conversion between the levels of acetaldehyde in the breath and blood alcohol level. This relationship is dependent on the enzymatic activity in the body. It is also difficult to predict the concentration of acetaldehyde in the exhaled breath of patients with dehydrogenase deficiency. A large part of the Asian population has this genetic mutation. In the article (P C Kamat et. al., "Measurement of Acetaldehyde in exhaled breath using a laser absorption spectrometer," Applied Optics, Vol. 46 pp. 3969-3975, 2007) a cryogenically cooled lead salts was used with an absorption cuvette of 100 m length for the measurement of acetaldehyde in exhaled breath. The wavelength was tuned to 5.79 µm, and the instrument sensitivity obtained was 80 ppb.

In U.S. Pat. No. 7,292,153, a system for remote measurement of acetaldehyde vapor to test the blood alcohol content is proposed. The system utilizes a monochromatic light source operating at 340 nanometers in the UV. It is not clear why this wavelength was chosen since acetaldehyde has a broad absorption feature centered around 290 nm, the absorption at 340 nm is around 8% of the maximum value. It is also unclear what fractional absorbance could be achieved in a remote sensing system operating in the UV. The broad acetaldehyde spectra around 290 nm does not permit the use of modulation techniques such as WMS to obtain sufficient sensitivity. The method proposed in application U.S. Pat. No. 7,292,153 is not sufficient to obtain adequate measurement sensitivity required to detect drunk drivers.

The above methods, besides the insufficient sensitivity and selectivity of the measurement of ethanol also do not allow the quantitative determination of ethanol concentration in the exhaled air but only observe its presence. For quantitative measurement of the concentration of ethanol in the breath it is necessary to simultaneously measure an additional gas component contained in the breath, the concentration of which is known from the general laws of biology, which dilution in the atmosphere is similar to the ethanol vapor in the breath. This allows to estimate the effective length of the absorption column and the dispersion of the exhaled air sample. Such methods have been proposed so far only for an on-board extraction equipment, that take a sample of the gas from one point inside the cabin. In the U.S. Pat. No. 7,279,132 and the patent application US2010/0188232 it is proposed to use carbon dioxide as a tracer gas to determine the amounts of other gases in the exhaled air measuring both gas components simultaneously using NDIR spectroscopy.

All of the known methods of determination of the concentration of alcohol vapor are inadequate. It is not possible, with up to now known methods, to remotely make precise measurement of trace amounts of alcohol vapor in the air exhaled by a human. Previous methods can only indicate its presence when the quantity in exhaled breath permitted by law is considerably exceeded. Using previous methods, there is also a significant risk of measurement errors due to the presence of other gases in the exhaled air or in the atmosphere.

The solution according to the present invention eliminates that inconvenience. The aim of the invention is to make the determination of trace amounts of alcohol vapor in breath possible, particularly the remote determination of alcohol vapor without interruption of the current activity of the person tested.

The essence of the invention consists of the fact that a beam of light, preferably generated by a laser light source with a wavelength corresponding to the absorption spectrum of alcohol, preferably in the wavelength range of 3.28-3.52 µm, or in one or several wavelength ranges of 6.49-7.46 µm, 7.74-8.33 µm, 8.84-10.10 µm, 10.7-12.00 µm, is sent across a measuring space. The light intensity is measured after beam passed through said measuring space, and then, based on spectral analysis of the dependence of the light intensity to the alcohol content in the measurement space, the concentration of alcohol vapor is determined.

It is advantageous that the wavelength of the light source is tuned to a wavelength range covering a sharp absorption feature of ethanol at a wavelength of 3.345 µm or 7.174 µm or 8.057 µm or 9.377 µm or 11.372 µm and that a part of and/or the whole of an absorption 'plateau', preferably located in close proximity of that sharp feature, is included in the measured spectrum.

It is also advantageous that, in addition the wavelength is tuned to a wavelength range covering a single absorption line or multiple absorption lines of a tracer gas, such as carbon dioxide and/or water vapor.

Furthermore, it is advantageous that while generating a beam of laser light having a wavelength corresponding to the absorption spectrum of ethanol, preferably at a wavelength around 3.345 µm, the wavelength is tuned over a range covering the whole or a part of a sharp absorption feature of ethanol at a wavelength of 3.345 µm. Said laser beam is then sent through the cabin of the vehicle, and then the intensity of the light after the beam passed through the measuring space is measured. Based on spectral analysis of the dependence of light intensity to the alcohol concentration, the concentration of alcohol vapor is determined.

Furthermore it is advantageous that the wavelength of the light source is tuned to a sharp absorption feature of ethanol at a wavelength of 3.345 µm, and that that the tuning range includes a part of or the whole of an absorption 'plateau' preferably located in proximity of the sharp absorption feature of ethanol.

It is also advantageous that immediately before the measurement the background signal, which contains the absorption signal from other atmospheric gases, the characteristics of the used light source and any distortion of the received light signal in the used receiving means, is recorded and removed from the measured spectrum.

It is advantageous that in addition the wavelength is tuned to a wavelength range covering a single absorption line or multiple absorption lines of a tracer gas, such as carbon dioxide and/or water vapor. The concentration of the tracer gas is used to determine the amount of exhaled breath.

Additionally it is advantageous that a second light source is used to emit a light beam with a wavelength corresponding to an absorption feature of a tracer gas such as carbon dioxide or water vapor, then said light beam is passed through the vehicle's passenger compartment containing a sample of exhaled air. The level of carbon dioxide or water vapor in the cabin of the vehicle is determined, based on the measurement of the level of light detected from the second source. The level of alcohol in the breath is then calculated using the ethanol concentration and the concentration of the tracer gas in the cabin.

In one implementation of the disclosed invention a modulated beam of light is generated using a wavelength corresponding to the absorption feature of ethanol, the absorption feature is included in the wavelength range of 3.28-3.52 µm, or within one or more of the wavelength ranges of 6.49-7.46 µm, 7.74-8.33 µm, 8.84-10.10 µm, 10.7-12.00 µm. The generated beam of light is then passed through a defined space containing exhaled air and the light passing through this space is measured and the level of ethanol vapor in the exhaled air is determined based on the level of light detected after passing through this space.

In another interrelated implementation the measurement of the spectral features of ethanol and the tracer gas is performed using the Wavelength Modulation Spectroscopy (WMS) method.

It is advantageous when a light beam of a wavelength corresponding to the absorption spectrum of a tracer gas, such as carbon dioxide or water vapor present in the exhaled air is generated. Said light beam is then passed through the space containing the sample of exhaled air. The intensity of light passing through this space is measured and the level of carbon dioxide and water vapor in the breath sample is determined based on the level of light detected. Since the level of carbon dioxide and water vapor in exhaled breath is known from established relationships in biology and medicine, this measurement can be used to determine the length of the absorption column and the dilution of the sample of exhaled air in the measuring space. The absolute level of ethanol vapor in the breath is then calculated by means of the ethanol absorption level and the tracer gas absorption level in the measuring space.

Moreover it is advantageous that after the determination of the level of alcohol vapor concentration, the information is supplied to a suitable display and/or other equipment for further processing.

One aspect of the device according to the invention is that it is equipped with a synchronizing-calculating module for determination of the concentration of ethanol vapor by means of the spectral analysis of the received detector signal. Said module is connected to the detector for detecting the light intensity from a light source that is configured to send a beam of light into the measuring space containing the sample of exhaled air. Said light source emits a beam of light in the wavelength range of 3.28-3.52 µm, or within one or more of the wavelength ranges of 6.49-7.46 µm, 7.74-8.33 µm, 8.84-10.10 µm, 10.7-12.00 µm.

In another interrelated implementation the light source is a tunable, single-mode semiconductor laser GaInAsSb/AlGaInAsSb.

In another interrelated implementation, the light source is a tunable quantum cascade laser (QCL).

In another interrelated implementation the light source is a tunable interband cascade laser—(ICL).

In another interrelated implementation the light source is a tunable vertical-cavity surface-emitting laser (VCSEL).

In another interrelated implementation the light source generates light by means of difference frequency generation (DFG), nonlinear mixing of the beams from two lasers.

It is advantageous when the light source is configured to emit a light beam with a wavelength of 3.345 µm or 7.174 µm or 8.057 µm or 9.377 µm or 11.372 µm, with the possibility of wavelength tuning through a sharp absorption feature of ethanol vapor, which occur at wavelengths of 3.345 µm or 7.174 µm or 8.057 µm or 9.377 µm or 11.372 µm.

Additionally it is advantageous when the light source is tuned over a wavelength range covering a single absorption line or multiple absorption lines of a trace gas, such as carbon dioxide and/or water vapor, in order to determine the absolute concentration of ethanol in the exhaled air.

In another interrelated implementation the disclosed device is equipped with an additional source of laser light at a wavelength corresponding to absorption lines of a tracer gas contained in the exhaled air, such as carbon dioxide or water vapor, in order to determine the absolute concentration of ethanol in the exhaled air.

It is advantageous when the device is configured to detect the presence of alcohol vapor in the passenger compartment of the vehicle, using a beam of light with a wavelength of 3.345 µm.

In one implementation, the transmitter and the receiver are located on opposite sides of the measuring space.

In another interrelated implementation the device is equipped with a retro reflector to redirect the beam to the receiver, wherein the transmitter and the receiver are on the same side of the measuring space.

The advantageous effect of the present invention is to improve the state of the art by greatly increasing the sensitivity and selectivity of a device for measuring ethanol vapor in exhaled air.

Figure 1B:
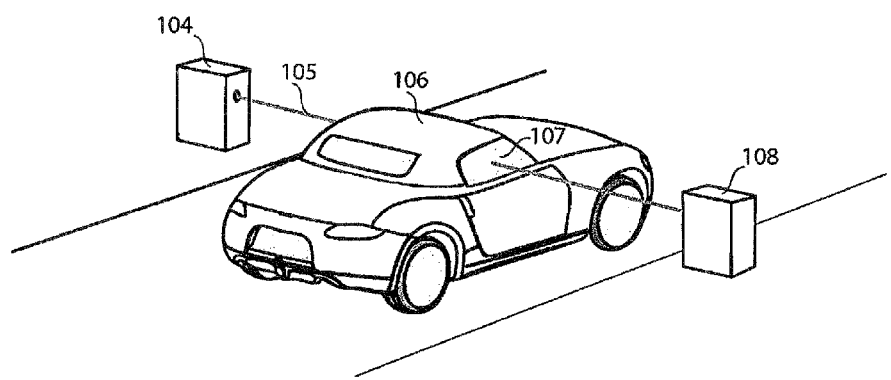
Figure 2A:
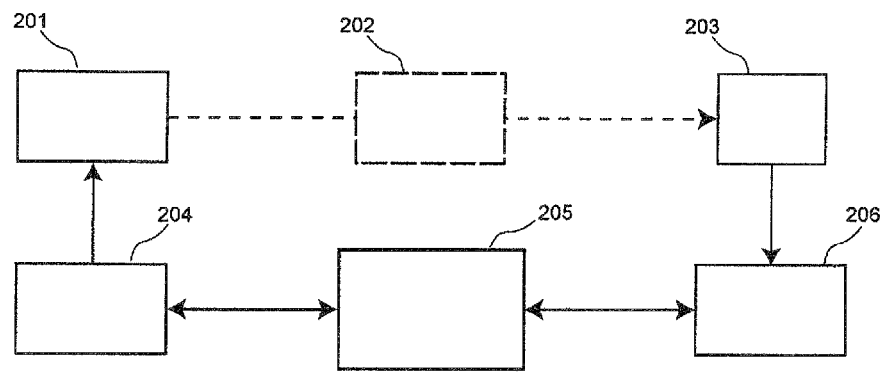
Figure 2B:
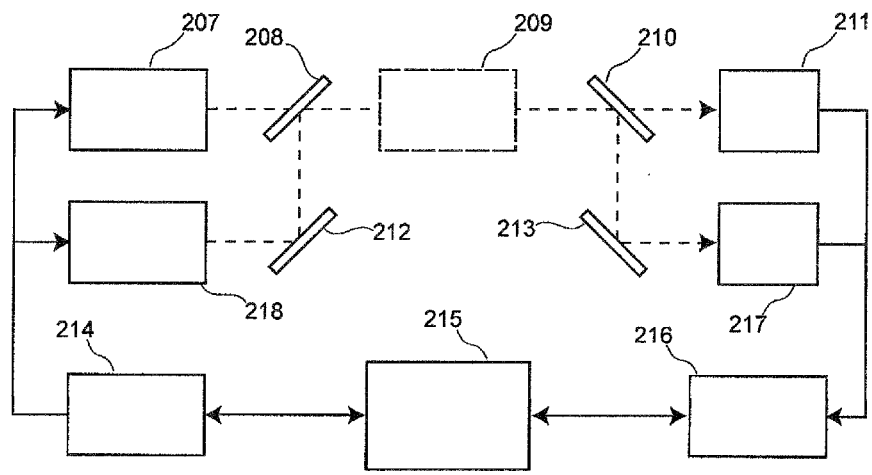
Figure 3A:
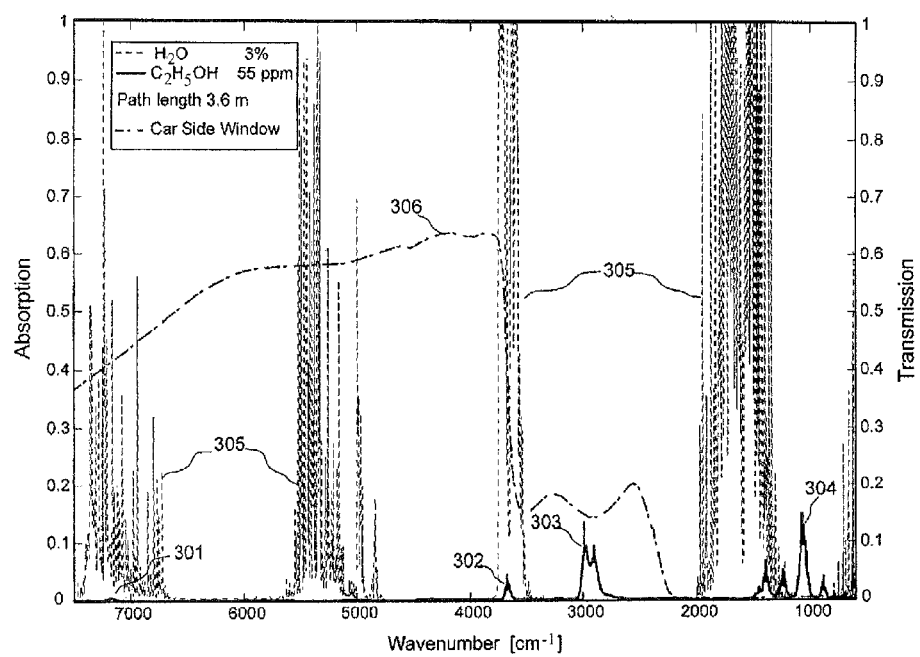
Figure 3B:
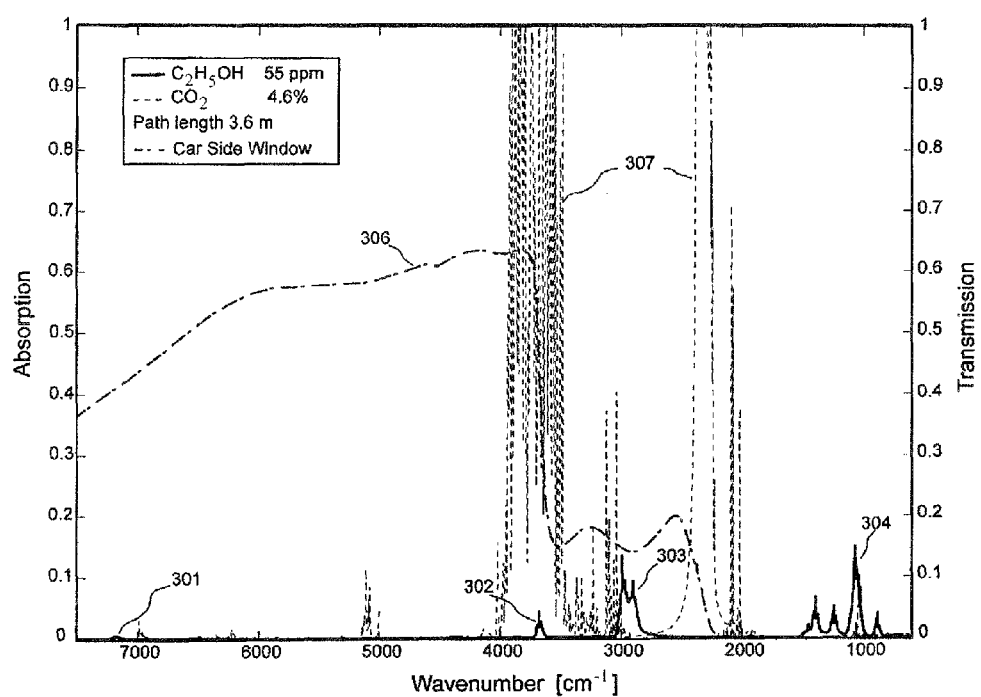
Figure 4:
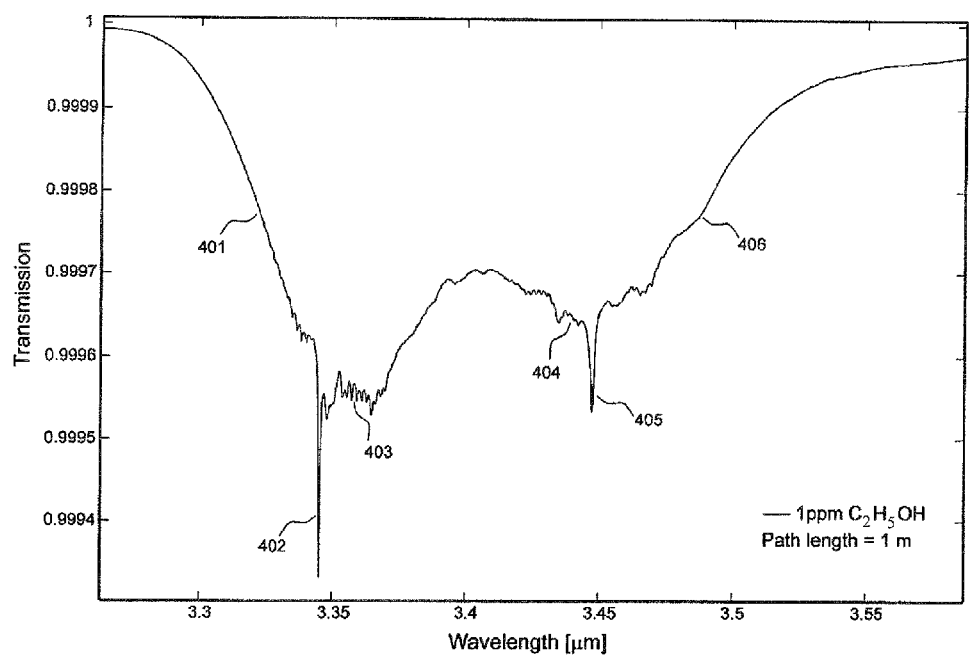
Figure 5:
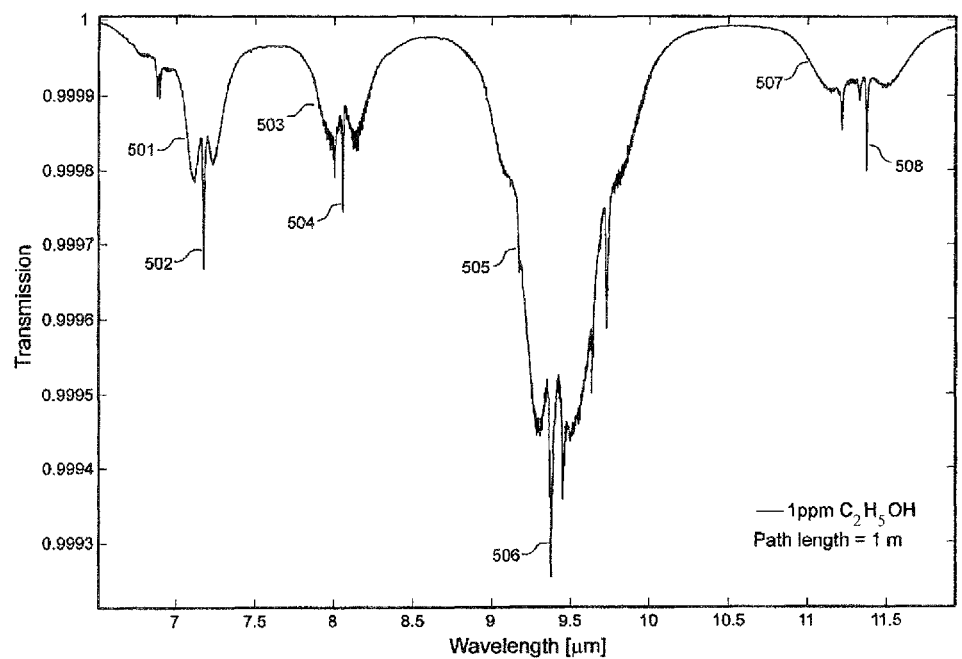
Figure 6:
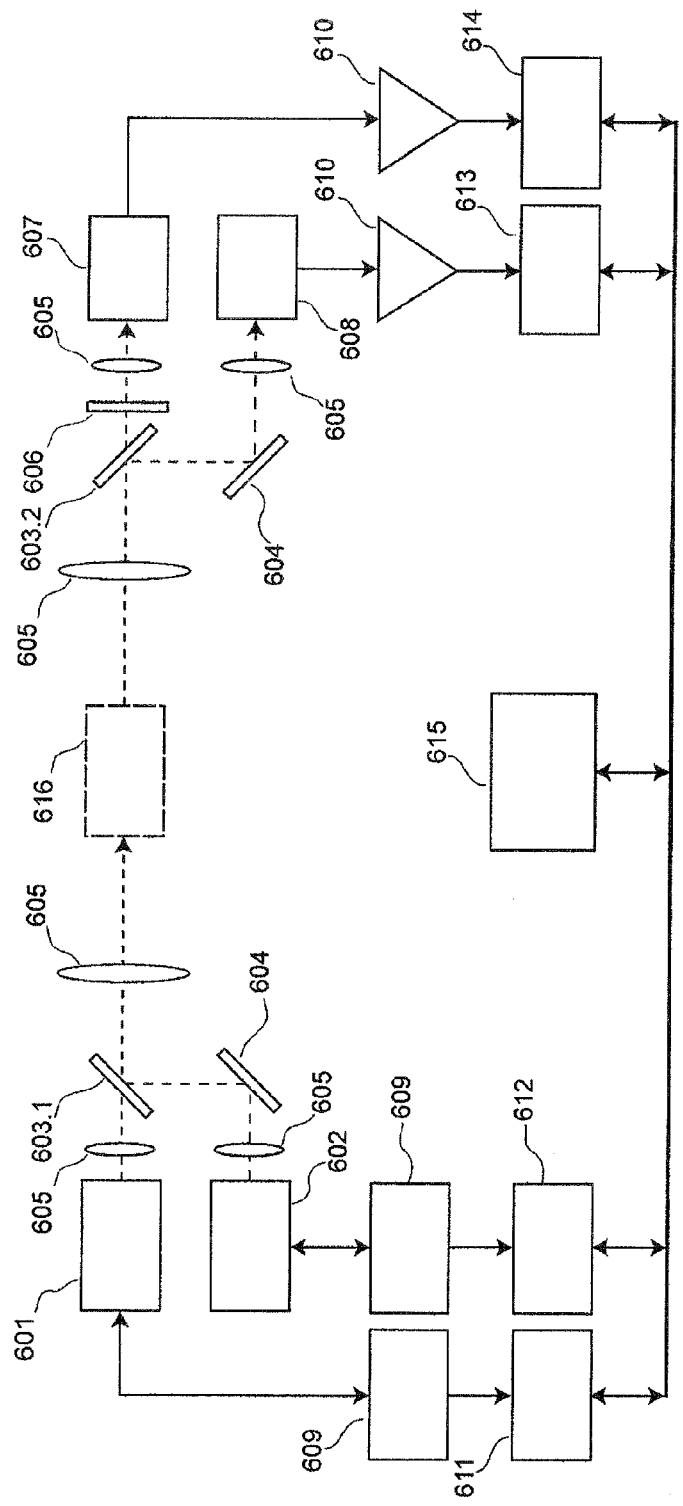

The invention is further explained with reference to the embodiments and the drawings in which the various figures show:

FIG. 1a—a system for control of the alcohol content in exhaled breath of employees before entering a workplace, FIG. 1b—a system for control of the alcohol content in exhaled breath of drivers in passing vehicles, FIG. 2a—a block diagram of the device to control the level of the alcohol vapor in an implementation with one laser, FIG. 2b—a block diagram as above but in an implementation with two lasers and a separate tracer gas detector, FIG. 3a—a spectrum of ethanol, a spectrum of water vapor and the optical transmission of a typical car window, FIG. 3b—a spectrum of ethanol, a spectrum of carbon dioxide and the optical transmission of a typical car window, FIG. 4—optical transmission through ethanol vapor in the wavelength region from 3.326 to 3.587 µm, the concentration of ethanol vapor is 1 ppm, FIG. 5—optical transmission through ethanol vapor in the wavelength region from 6.512 to 11.936 µm, the concentration of ethanol vapor is 1 ppm, FIG. 6—a block diagram as shown in FIG. 2b but in an implementation with two lasers, a tracer gas detector with separate preamplifier and signal processing, two modulation waveform generators and two laser drivers.

More specifically, the present invention relates to a technique for remotely determining the level of ethanol in the exhaled breath of an intoxicated person which is entering a parking garage to retrieve his vehicle or entering an area specifically designated to be free of any alcohol intoxicated persons such as a critical area of a workplace as illustrated in FIG. 1a, where the laser 101 sends a beam 102 to the detector 103, across the opening of a door, through which worker passes. Another application of the invention is to monitor the concentration of ethanol vapor in the breath of a person in the cabin of a motor vehicle, as shown in FIG. 1b. Another aspect of the invention is to monitor the concentration of ethanol in the exhaled breath of a person confined within the passenger compartment of a motor vehicle as shown in FIG. 1b. In this case, the laser 104 and detector 108 are arranged on both sides of the road, and the beam 105 passes through the measuring space 106 and the car window 107, and reaches the detector 108.

The current invention utilizes optical absorption spectroscopy to measure the concentration of ethanol vapor in exhaled breath. The light source can be a conventional hot filament lamp, a light emitting diode (LED), a laser or any other suitable emitter covering the wavelength of interest. The laser 101 offers the advantage that it generates a beam 102 of monochromatic coherent light that can be propagated over substantial path lengths. By measuring the amount of light absorbed by the gaseous sample at wavelengths specific for the gas species of interest, the concentration of the said specie can be accurately determined.

In a first aspect illustrated in FIG. 2a a laser 201 is connected to a laser driver 204, and a photodetector 203 is connected to a signal processing module 206. A synchronizing-calculating module 205 is connected both to the signal processing module 206 and the laser driver 204. A laser light source 201 that emits at a chosen wavelength sends a light beam through a measuring space 202 where the ethanol vapor resides, to a photodetector 203 that measures the light intensity. Preferable this detector is an InAs/InAsSbP heterostructure detector. The laser driver 204 provides the driving current to the laser and controls the temperature in order to reach the correct wavelength of the emitted light. This module also includes any circuit necessary to scan or modulate the emitted laser wavelength across an absorption feature of the gas. The signal from the photodetector 203 is connected to a signal processing module 206 that extract information about the absorption feature of the gas. A synchronizing and calculating module 205 synchronizes the signals to the laser and calculates the ethanol concentration from the spectra received from the signal processing module 206. The apparatus may include means to measure a known concentration of a tracer gas such as water vapor or carbon dioxide from the exhaled breath in order to determine the length of the absorption column and the dilution of the sample of exhaled air in the measuring space. If the absorption features of ethanol and the tracer gas is close in wavelength both ethanol and the tracer gas can be measured using one laser, as shown in FIG. 2a. The absolute concentration of ethanol in the exhaled breath can then be determined using the measured concentration of ethanol and the tracer gas. The concentration of excess gas vapor, such as water vapor or carbon dioxide, are constant and known from established relationships in biology and medicine, and may therefore be used to determine the absorption column of the sample of exhaled air and the degree of dilution of the measured gas. This procedure will be described in more detail further on in the text.

In a second interrelated aspect shown in FIG. 2b, an apparatus may include a second laser to measure a tracer gas such as water vapor or carbon dioxide from the exhaled breath in order to determine the volume of said exhaled breath in the measuring space 209. The beams from the two lasers 207 and 218 are combined through the set: beam combiner 208-mirror 212. The beam is sent through the measuring area 209 to the set of two detectors: photodetector 211 and tracer gas detector 217 through the set: beam splitter 210-mirror 213. The output from the detectors 211 and 217 is connected to a signal processing module 216, and a synchronizing-calculating module 215. The block of lasers 207 and 218 are connected to the laser driver and control module 214. The first laser light source 207 emits at a chosen wavelength to measure ethanol, and then sends the beam through the measuring space 209 where the ethanol vapor resides 209 and a photodetector 211 that measures the light intensity after the beam passing through this space. Said detector is configured to quantify the amount of light at a wavelength used to detect ethanol. A second laser light source 218 emitting at a chosen wavelength to measure a tracer gas such as $CO_2$ or $H_2O$ is added to the system. The lasers are controlled by the laser driver and control module 214. The temperature and the bias current of each laser is controlled separately. The scanning and modulation method for each laser can be chosen separately. Optical elements such as mirror 212, beam combiner 208 and is used to transmit said second laser beam over the same path as the first beam. The optical elements beam combiner 210 and mirror 213 is used to separate said second laser beam onto the reference gas detector 217. In various optional aspects the optical beams can be configured by a mechanical scanner an acousto-optical scanner, an electro-optical scanner or a diffractive optical element. The optical beams may optionally be transmitted parallel to the first beam at any suitable distance between said beams.

The detection mean that is quantifying the light passing through the gas sample 209 is configured to separately determine the light at the wavelength chosen for ethanol detection and the wavelength chosen to detect the tracer gas. In one aspects this can be done by using two separate detector elements and an optical arrangement to separate the two wavelengths. The arrangement can be a beam splitter 210 and a mirror 213. The received light is then quantified by two detectors, one for each wavelength band. Preferably the detector for the wavelength chosen for ethanol detection 211 is an InAs/InAsSbP heterostructure detector. The detector chosen for detecting the tracer gas is preferable an InGaAs detector 217. In various optional aspects an arrangement with optical filters well known in the art can be used for separating the wavelength channels. In other aspects a two color detector made by sandwiching two separate semiconductor materials with different spectral sensitivity can be used. The electrical signal from the detector or detectors are fed to a signal processing module 216 in order to retrieve the absorption parameters and subsequently to the synchronizing-calculating module 215, where the calculation of the concentration of ethanol and the tracer gas is made based on the spectra.

Interference among constituents in a gas mixture occurs when the spectral absorption features of the gas of interest overlaps other similar absorption features of other gases in the path. That is, the light will be absorbed in the same or nearly the same way as another gas present in the absorption path. These interferences can often be the limiting factor determining the sensitivity of the measurement. Many spectral regions are rich with absorption features from various gas components which interfere with the absorption from the ethanol molecule. There are smaller molecules with well-resolved rotational-vibrational absorption spectral lines like water vapor and carbon dioxide and larger molecules with higher molecular weight like hydrocarbons where the rotational transitions overlap into broader absorption features. Carbon dioxide and water vapor limits the choice of spectral regions suitable for measurement over open atmospheric paths as shown in FIG. 3a and FIG. 3b. In these calculations the water concentration in the ambient atmosphere is between 0.5 and 4% while in exhaled breath it is typically around 5%. The $CO_2$ concentration in the atmosphere has a typical background level of 390 ppm while in exhaled breath it is typically around 4.6%. Ethanol absorbs light at nearly the same wavelengths as $H_2O$ but as can be seen in FIG. 3a there are atmospheric windows where the water absorption is very small and where the ethanol molecule has absorption bands namely the 3.28-3.52 µm 303 and the 10.7-12.00 µm 304 bands. Carbon dioxide has major infrared absorption bands around 4.26 µm and 2.7 µm which blocks any transmitted laser radiation. There is a prominent ethanol absorption bands 301 and 302 at the wavelength of 1.38-1.41 µm and 2.68-2.78 µm but they are totally unsuited for this application due to the strong interference from both $CO_2$ and $H_2O$. From FIG. 3a and FIG. 3b it is clear that the preferred wavelength ranges chosen for ethanol detection in the atmosphere are 3.28-3.52 µm (3049-2841 cm$^{-1}$), 6.49-7.46 µm (1541-1340 cm$^{-1}$), 7.74-8.33 µm (1292-1201 cm$^{-1}$), 8.84-10.10 µm (1131-990 cm$^{-1}$) and 10.7-12.00 µm (935-833 cm$^{-1}$).

For the application of detecting ethanol in the exhaled breath of a person occupying the passenger compartment of a vehicle the window of said vehicle has to transmit enough light so that the beam can be passed through the vehicle and be detected by a suitable configured detector. In FIG. 3a and FIG. 3b the optical transmission of a side car window 306 has been included. From this wavelength plot we can conclude that the wavelength range around 3.28-3.52 µm 303 is an excellent choice since it has low level of optical interferences from carbon dioxide 307 and water vapor 305 and the optical transmission through the car window is good. For detecting the ethanol concentration in the exhaled breath from alcohol intoxicated persons in areas not restricted by the transmission of any windows the wavelength region around 10 µm 304 is also an excellent choice.

The measurement of the concentration of higher-molecular-weight gases, like ethanol, using tunable laser spectroscopy is especially challenging since these gases generally do not show resolved rotational vibrational absorption lines and have an absorption spectral width greater than the tuning range of any presently available tunable semiconductor diode laser that is not using an external cavity. In the spectral regions of interest for ethanol detection there is also an abundance of other larger molecules with such unresolved spectral features. However, as shown in FIG. 4 and FIG. 5 the absorption spectra of ethanol have well defined sharp features that can be used to separate out this gas component from any other interfering broad band absorber occupying the same spectral interval, such as acetaldehyde, acetone, formaldehyde or methanol. It is evident that the broad absorption feature outside the sharp feature will contribute to the overall absorption of the optical radiation. However, by doing a simultaneous measurement of this absorption level and use this value to normalize the received optical power, a correct value of the ethanol concentration will be obtained. This is no limitation since it is always necessary to normalize the received optical radiation level due to losses such as absorption due to fog and dust and in optical elements such as lenses and windows. The method of extraction of the normalized ethanol concentration is described below.

Beer-Lambert law describes the resulting absorption of laser radiation along a measurement path attenuated by scattering (due to dust particles) and by one or several of gaseous of species in the path:

$$I_R = T_0 I_0 \exp\left[-\left(\sigma + \sum_i c_i \alpha_i\right) L\right] = I_0 T \exp\left[-\sum_i c_i \alpha_i L\right]$$

where $T_0$ is the sum of optical losses in the system, $I_0$ is the transmitted laser intensity, $\sigma$ is the extinction coefficient due to scattering, $c_i$ is the concentration of gas species i, $\alpha_i$ is the absorption coefficient for species i and L is the measurement path length. Define $T=T_0 \exp(-\sigma L)$ as the total transmission due to the optical losses and extinction by dust particles. For the absorption from a single species such as ethanol we can then further write the following expression:

$$I_R = I_0 T T_\alpha(c) \exp[-c\alpha(\nu)L]$$

where we introduced $T_\alpha(c)$—the transmission due to broadband absorption by molecules in the gas matrix. Since the width of the laser wavelength scan is on the order of a few wavenumbers, we can assume that the broadband molecular absorption is independent on the laser frequency and will only depend on the gas matrix concentration. As alluded to above the 3-4 µm wavelength band have many broad absorption features due to various hydrocarbons. This also includes broadband absorption contributions from ethanol vapor itself why $T_\alpha(c)$ also is a function of the ethanol concentration.

The contribution of the sharp ethanol feature 402 to the whole absorption signal, on the other hand depends strongly on the laser frequency, $\nu$, and thus can be clearly distinguished from any broadband absorption, 403. By taking the ratio, between the received signal at the sharp feature 402 and at the broadband absorption 403 in FIG. 4, we obtain the following relation:

$$S_{etOH} = \frac{I_0 T T_\alpha(c) \exp[-c\alpha(\nu)L]}{I_0 T T_\alpha(c)} \approx [1 - c\alpha(\nu)L]$$

where in the last step we have used the fact that the absorption from ethanol is small. As we can see the above procedure enables us to normalize the ethanol absorption signal against both the total transmission T and the broadband absorption in the region of the "plateau" absorption $T_\alpha(c)$ at 403 and the changes in the light intensity from the source $I_0$. Therefore, the normalized signal depends only on the ethanol concentration in the compartment c, (measured at the sharp feature 3.345 μm, 402) and the interaction length, L. If the wavelength of the used laser is widely tunable, the "plateau" region can be selected at a different wavelength than 403 as shown in FIG. 4. A prerequisite for the selection of the spectral "plateau" is that the absorption spectrum of ethanol in this area is flat and the strength of absorption is as small as possible, preferably zero. An example of such an alternative "plateau" is a region around a wavelength of 3.326 μm, at the beginning of the transmission spectra shown in FIG. 4.

In the case when the gas forms a cloud with inhomogeneous concentration, the above formula takes the following form:

$$S_{etOH} = 1 - c_{BrAC}\alpha(\nu)\int_L \rho(z)dz$$

$c_{BrAC}$ is the concentration of ethanol in exhaled breath and $\rho(z)$ is the distribution of ethanol molecules in air along the measured column. The integral $$\int_L \rho(z)dz$$

cannot be estimated analytically because the sample size and its dilution is unknown however we can find it by means of a simultaneous measurement of above mentioned tracer gas. The tracer gas can be either $H_2O$ or $CO_2$, both having known concentration in exhaled breath and both diluting in air in the same way as the ethanol molecules do [1]. We can write the following relation for the tracer gas:

$$S_{tracer} = 1 - c_{tracer}\alpha_{tracer}(\nu)\int_L \rho(z)dz$$

After removing the constant offset from both the ethanol and the tracer gas signals and taking the ratio we obtain the final formula for the ethanol concentration in exhaled breath as:

$$c_{BrAC} = \frac{c_{tracer}}{S_{tracer}}S_{EtOH}$$

The signals $S_{EtOH}$ and $S_{tracer}$ can be measured using either one laser in a setup shown in FIG. 2a (if the absorption lines of ethanol and the tracer gas are close in optical frequency) or by means two separate lasers, one for ethanol and the other for the tracer gas, see the setup shown in FIG. 2b.

In order to increase the accuracy and detection limit of the instrument probing the alcohol content in the vehicle compartments, an additional background removal function (or zeroing) can be applied before the actual measurement is performed. The background signal is recorded while the laser beam is not obscured by any vehicle and is then normalized due to the optical losses in the system and the subtracted from the analytical received signal measured when the vehicle passed the beam. The background signal is normalized in the same way as the analytical signal, described above. The background signal therefore contains the absorption information from atmospheric gases, mainly $H_2O$, that are absorbed over the laser beam path. Depending on the weather conditions, the water vapor level can be quite high so it can obscure the absorption signal from ethanol. Moreover, the background signal also contains the laser intensity characteristics as well as any intensity distortions that can originate in the optomechanical setup (due to interference effects, so called etalon effects) that also normally disturb the ethanol signal. Therefore such a background subtraction method greatly improves the detection limit and accuracy of the measurement.

The current invention preferably utilizes a laser light source for the absorption spectroscopy, thereby enabling an efficient detection of the sharp features in the spectra and minimizing the interference from other gases due to the narrow spectral line width of the source. The spatial coherence of the laser also enables it to be propagated over a long atmospheric path enabling stand-off detection of ethanol. The preferred laser type in this case is a tunable type-I DFB laser (L. Naehle et. al. "Continuous-wave operation of type-I quantum well DFB laser diodes emitting in 3.4 μm wavelength range around room temperature", *Electronic Letters* 47, p. 46-47, (2011)). Alternatively, a tunable type-II interband cascade diode laser (ICL) operating room temperature in the 3.3-3.7 μm wavelength range can be used. In addition other types of light sources can be used such as an intraband quantum cascade laser (QCL) or a vertical-cavity surface-emitting laser (VCSEL). In another embodiment a difference-frequency generation laser (DFG) can be utilized. However, the DFG adds another level of complexity and cost since it utilizes two single mode lasers operating in the near infrared that are mixed in a non-linear optical crystal in order to generate laser radiation a the wavelength 3.5 μm.

The disclosed method for determination of the ethanol vapor concentration consists a definitive improvement over previous art by performing the measurements within one or several of the wavelength ranges of 3.28-3.52 μm (ethanol absorption band of 401) with a sharp absorption feature at 402 (3.345 μm), 6.49-7.46 μm (ethanol absorption band of 501) with a sharp absorption feature at 502 (7.174 μm), 7.74-8.33 μm (ethanol absorption band of 503) with a sharp absorption feature 504 (8.057 μm), 8.84-10.10 μm (ethanol absorption band of 505) with the sharp absorption feature 506 (9.337 μm) and 10.7-12.00 μm (ethanol absorption band of 507) with the sharp absorption feature 508 (11.372 μm), which all have minimal interferences from water or carbon dioxide and where the ethanol molecule has a high line strength. In FIG. 4. and FIG. 5 suitable regions for laser based measurement have been indicated. Differential absorption can be utilized for ethanol detection by tuning a light source in wavelength over a part of the slope in the spectra as exemplified by wavelength regions 401 and 501. In each of the chosen wavelength bands there are sharp absorption features: sharp absorption feature 402 of 3.345 μm with absorption "plateau" 403, sharp absorption feature 405 of 3,447 μm with absorption "plateau" 404 or sharp absorption feature 502 of 7,174 μm, that can be used to discriminate the absorption from the ethanol molecule from absorption from other broadband absorbers. The current invention utilizes one or several such sharp features by scanning the laser wavelength over said sharp features. As an example we can use the feature 402 to detect ethanol and the region around 403 for normalization purposes. The total wavelength scan to cover the region 402 and 403 can be covered with a single-mode semiconductor laser such as the GaInAsSb/AlGaInAsSb DFB, used in this invention.

The laser light is then passed through a volume containing the exhaled breath. This gas volume can be at a substantial distance from the measurement apparatus since the nature of the laser light makes it possible to propagate the beam over long atmospheric paths. The light beam is subsequently detected with a detector configured to receive light from the source and the generated electrical signal is fed to an appropriate signal processing mean. For the detection of the received optical radiation the current invention preferably utilizes a photodiode based on the InAs/InAsSbP heterostructure optimized for operation in the midinfrared wavelength region. For operation at shorter wavelengths an InGaAs or Si detector is used. For wavelengths above the 3-4 µm wavelength region preferably a Mercury Cadmium Telluride (MCT) detector with or without thermo electric cooling can be used. However any detector configured to receive light from the light source can be used.

In order to improve the detection sensitivity a technique with rapid wavelength scanning of the laser with direct absorption detection and sweep integration can be employed. The sweep integration technique is a high frequency version of the technique that was pioneered by Jennings et. al. "Absolute line strengths in v4, 12CH4: a dual-beam diode laser spectrometer with sweep integration", Appl. Opt. 19, 2695 (1980)). Application of the rapid scanning is also necessary in order to reach the short signal acquisition times that are required to probe the ethanol levels in compartments of moving vehicles. Assuming a speed of 110 km/h and a length of the side window of 1 m, the acquisition time for a complete spectrum has to be on the order of 0.03 seconds. In order to reach sufficient signal-to-noise ratio of the measured signal, the scanning frequency therefore has to be on the order of several kHz. The direct absorption technique retain the true shape of the absorption line and provides a mean to perform calibrated measurements by including enough of the region around the absorption feature. The direct absorption technique also decrease the requirement on the laser wavelength modulation capability. The sharp features of the ethanol molecule typically have a line width 10-20 times larger than that of a smaller molecule like $CO_2$ or $H_2O$, which requires the use of higher modulation amplitudes to completely spectrally cover the whole absorption line.

In an interrelated aspect of this invention a technique called harmonic or wavelength modulation spectroscopy (WMS) can be used to improve the sensitivity. This technique is especially well suited for the optional detection channel for a tracer gas like $CO_2$ or $H_2O$ since these absorption lines are narrow allowing the use of wavelength modulation. The inventors have successfully demonstrated the use of the WMS technique to detect the sharp ethanol absorption feature around 3.345 µm. The advantage of the technique is the removal of any constant absorption and reduction of the 1/f noise in the system. However in the application with stand-off detection of ethanol vapor in a passing vehicle the response time necessary makes WMS less favorable.

The disclosed device for remote detection of the sobriety of persons in a defined area like a work place would monitor the level of alcohol vapor in the exhaled breath without the need for disruption of normal routines. The detection is made in real-time and the information could be connected to a general monitoring and surveillance system. The disclosed device used for remote detection of the driver sobriety would greatly increase the detection rate without the need for disruption of the traffic. The detection is made in real time without the need to reduce the speed of the vehicle below that of the general speed limit. The system of the present invention is capable of detecting the presence of ethanol vapor at concentrations down to 0.5 parts per million (0.001 mg/L). This level corresponds to the expected level of alcohol vapor in the inner compartment of a vehicle occupied by a person under the influence of alcohol in excess of the legal limit. The limit for ethanol in exhaled breath in many European countries such as Poland and Sweden is 0.1 mg/L which corresponds to 53 parts per million. The exhaled alcohol vapor will be diluted by the gas volume in the passenger compartment and the dilution will depend of the use of forced ventilation. However the dilution can be accurately quantified using a simultaneous measurement of a tracer gas such as $CO_2$.

As shown in FIG. 6, in the method of automatic remote detection of alcohol vapor in the air uses wavelength modulation of the propagated light wave. For the remote measurement the system utilizes a modulated laser 601, of the GaInAsSb/AlGaInAsSb type, tuned to the ethanol absorption feature 402 at the wavelength of 3.345 µm. The laser 601 is locked to this wavelength by the use of an active temperature control of the laser chip temperature and laser bias current 609. The emitted laser beam is collimated by a lens system 605. A second laser source 602 is used to detect the $CO_2$ content in the exhaled breath "plume". This laser is tuned to the $CO_2$ absorption line at 1.5786 µm by the use of an active temperature control of the laser chip temperature and laser bias current 609. The beams from the two lasers are combined in an optical arrangement comprising a mirror 604 and a beamsplitter 603.1. The transmitter emits a collimated coherent optical beam through a volume of air containing the exhaled carbon dioxide and ethanol vapor 616.

The received collimated laser beam comprising radiation at 3.345 µm and 1.5786 µm is separated and focused onto separate detectors by a lens combination 605, a beamsplitter 603.2, an optional optical filter 606 and a mirror 604. The detection of the signal take place on the other side of the measuring area 616. The optical absorption by the ethanol plume at 3.345 µm is detected by a photo diode based on an InAs/InAsSbP heterostructure 607. The laser radiation absorbed by the carbon dioxide absorption line at 1.58 µm is detected by an InGaAs photo diode 608. The electrical signals from the detectors are amplified in two separate trans-impedance amplifiers 610 (TIA) and fed to two signal processing modules 613 for carbon dioxide and 614 for ethanol. The output from the signal processing can be used for display or record the detected levels of ethanol molecules. The synchronizing-calculating module 615 enables the system to be operated autonomous and unattended. This module also synchronizes the modulation waveform generators, 611 for the 3.345 µm laser and 612 for the 1.5786 µm laser respectively.

The absolute alcohol concentration in the exhaled breath is calculated by the information processing and control using information derived from the recorded ethanol and carbon dioxide spectra, according to the previously derived formula:

$$c_{BrAC} = \frac{c_{tracer}}{S_{tracer}} S_{EtOH}$$

In addition, to increase the system sensitivity and eliminate interference by other gases in the atmosphere and other optical or electrical interference in the system (interferences from the characteristics of the laser and the optical system) during propagation of the beam to the area of measurement, such as a vehicle cabin, previously described method of removing the background (zeroing) is used.

THE LIST OF INDICATIONS IN THE DRAWING

FIG. 1b
- 104—laser
- 105—beam
- 106—measuring space
- 107—car window glass
- 108—detector FIG. 2a
- 201—laser
- 202—measuring space
- 203—photodetector
- 204—laser driver
- 205—synchronizing-calculating module 206—signal processing module FIG. 2b
- 207—the first laser
- 208—beam combiner
- 209—examined area
- 210—beam splitter
- 211—photodetector
- 212—mirror
- 213—mirror
- 214—control module
- 215—synchronizing-calculating module
- 216—signal processing module
- 217—tracer gas detector
- 218—second laser FIG. 3a
- 301—ethanol absorption band 1.38-1.41 μm (range described in the prior art and used in US2003160173)
- 302—ethanol absorption band 2.6-2.78 8 μm (range described in the prior art and proposed for example in the application JP2000230900)
- 303—ethanol absorption band 3.28-3.52 μm
- 304—ethanol absorption band 10.7-12.00 μm
- 305—absorption spectrum of water vapor
- 306—optical transmission of side car window FIG. 3b
- 301—ethanol absorption band 1.38-1.41 μm (range described in the prior art and used in US2003160173)
- 302—ethanol absorption band 2.6-2.78 8 μm (range described in the prior art and proposed for example in the application JP2000230900)
- 303—ethanol absorption band 3.28-3.52 μm
- 304—ethanol absorption band 10.7-12.00 μm
- 306—optical transmission of side car window
- 307—carbon dioxide absorption spectrum FIG. 4
- 401—ethanol absorption band 3.28-3.52 μm
- 402—sharp absorption feature of 3.345 μm
- 403—absorption "plateau" (to normalize the signal from the sharp feature 402)
- 404—absorption "plateau" (to normalize the signal from the sharp feature 405)
- 405—sharp absorption feature of 3.447 μm FIG. 5
- 501—ethanol absorption band of 6.49-7.46 μm
- 502—sharp absorption feature of 7.174 μm
- 503—ethanol absorption band of 7.74-8.33 μm
- 504—sharp absorption feature of 8,057 μm
- 505—ethanol absorption band of 8.84-10.10 μm
- 506—sharp absorption feature of 9.377 μm
- 507—ethanol absorption band of 10.7-12.00 μm
- 508—sharp absorption feature of 11.372 μm FIG. 6
- 601—tunable single-mode laser
- 602—single-mode tracer gas laser
- 603.1—beam combiner
- 603.2—beam splitter
- 604—mirror
- 605—lens system
- 606—optical filter
- 607—photodiode
- 608—photodiode
- 609—current/temperature driver
- 610—amplifier
- 611—modulation waveform generator
- 612—modulation waveform generator
- 613—signal processing module
- 614—signal processing module
- 615—synchronizing-calculating module
- 616—measuring space

LIST OF CITED PUBLICATIONS

Patents

| | | |
|---|---|---|
| 1. | U.S. Pat. No. 7,095,501 | Lambert, et al. |
| 2. | U.S. Pat. No. 7,279,132 | Sultan, et al. |
| 3. | U.S. patent application 2010/0188232 A1 | Lambert, et. al. |
| 4. | U.S. Pat. No. 5,907,407 | Atkinson, et. al. |
| 5. | PL 389627 Patent application | Mierczyk, et. al |
| 6. | U.S. Pat. No. 5,349,187 | Azzazy, et. al. |
| 7. | U.S. Pat. No. 7,292,153 | Ahmed, et. al |
| 8. | U.S. patent application 2003/160173 A1 | Ershov, et. al. |
| 9. | JP 2000-230900 (A) | Nishida |

Other Publications

1. B. Hök, H. Pettersson, A. Kaisdotter Andersson, S. Haasl, P. Akerlund, "Breath Analyzer for Alcolocks and Screening Devices," IEEE Sensors Journal, 10, pp. 10-15, (2009).
2. Beitel G A, Sharp M C, Glauz W D., "Probability of arrest while driving under the influence of alcohol," Inj Prev. June, 6(2), pp. 158-61, (2000).
3. T. A. Alobadi and D. W. Hill, "A helium-neon laser infrared analyzer for alcohol vapour in the breath," Journal of Physics E: Scientific Instruments, 8, pp. 30-32 (1975).
4. M. Azzazy, T. Chau, M. Wu, and T. Tanbun-Ek, "Remote sensor to detect alcohol impaired drivers," IEEE-Laser and Electro-Optics Society Annual Meeting, 2, pp. 320-321, (1995).
5. A. Nadezhdinskii, A. Berezin, Yu. Bugoslavsky, O. Ershov, and V. Kutnyak, "Application of near-IR diode lasers for measurement of ethanol vapor," Spectrochimica Acta Part A, 55, pp. 2049-2055, (1999).
6. A. Berezin, O. V. Ershov and A. I. Nadezhdinskii, "Trace complex-molecule detection using near-IR diode lasers", Applied Physics B, 75, pp. 203-214, (2002).
7. M. Schuetz, J. Bufton and C. R. Prasad, "A mid-IR DIAL system using interband cascade laser diodes", Proceedings of OSA/CLEO, paper JThD88, (2007).
8. K. Mitsubayashi, H. Matsunaga, G. Nishio, S. Toda and Y. Nakanishi, "Bioelectric sniffers for ethanol and acetaldehyde in breath after drinking", Biosensors and Bioelectronics, 20, pp. 1573-1579, (2005).
9. P. C. Kamat, C. B. Roller, K. Namjou, J. D. Jeffers, A. Faramarzallan, R. Salas and P. J. McCann, "Measurement of acetaldehyde in exhaled breath using a laser absorption spectrometer," Applied Optics, 46, pp. 3969-3975, (2007).

10. L. Naehle, S. Belahsene, M. von. Edlinger, M. Fischer, G. Boissier, P. Grech, G. Narcy, A. Vicet, Y. Rouillard, J. Koeth and L. Worschech, "Continuous-wave operation of type-I quantum well DFB laser diodes emitting in 3,4 μm wavelength range around room temperature", *ELECTRONICS LETTERS*, 47, p. 46-47, (2011).
11. William Bewley, Chadwick Canedy, Chul Soo Kim, Mijin Kim, J. Ryan Lindle, Joshua Abell, Igor Vurgaftman and Jerry Meyer, "Ridge-width dependence of midinfrared interband cascade laser characteristics", *Opt. Eng.* 49, 111116, (2010).
12. D. E. Jennings, "Absolute line strengths in $v_4$, $^{12}CH_4$: a dual-beam diode laser spectrometer with sweep integration," Appl. Opt. 19, 2695-2700, (1980)

What is claimed is:

1. A method for remote detection of alcohol vapor in the atmosphere, useful for determination of a concentration of ethanol vapor in air exhaled by humans, comprising
    generating from a laser light source a beam of laser light with a wavelength corresponding to the absorption spectrum of alcohol in a wavelength range of 3.28-3.52 μm, or in one or several wavelength ranges of 6.49-7.46 μm, 7.74-8.33 μm, 8.84-10.10 μm, and 10.7-12.00 μm,
    sending the laser light beam outside of a device in which the laser light source is housed and across a measurement space outside and separate from the device, the laser light beam being received by a detector,
    subsequently measuring a light intensity of the laser light after the beam has passed through the measurement space and has been received by the detector, and
    subsequently, based on spectral analysis of the dependence of the measured light intensity on an alcohol level, determining a concentration of alcohol vapor in the measurement space.

2. The method according to claim 1, wherein the wavelength of the laser light source is tuned over a wavelength range covering a sharp absorption feature of ethanol at a wavelength of 3.345 μm or 7.174 μm or 8.057 μm or 9.377 μm or 11.372 μm, and a part of and/or a whole of an absorption 'plateau', located in close proximity of the sharp absorption feature.

3. The method according to claim 2, wherein the wavelength is further tuned over a wavelength range covering a single absorption line or multiple absorption lines of a tracer gas selected from the group consisting of carbon dioxide and water vapor used to measure an amount of exhaled breath.

4. The method according to claim 1, wherein after the determining of the alcohol vapor concentration, the information is supplied to a suitable display and/or other equipment for further processing.

5. The method according to claim 1, wherein the laser light source and the detector are located on opposite sides of the measurement space.

6. The method according to claim 1, wherein the laser light source and the detector are on a same side of the measurement space and a retro-reflector that redirects the laser light beam to the detector is located on an opposite side of the measurement space.

7. The method according to claim 1, wherein the measurement space comprises a vehicle passenger cabin.

8. A method of remote detection of ethanol vapor concentration in the exhaled breath from persons inside a cabin of a vehicle, comprising generating a beam of laser light at a wavelength range around 3.345 μm, said wavelength range covering a whole or a part of a sharp absorption feature of ethanol at a wavelength of 3.345 μm, sending the laser light beam through the cabin of the vehicle, and then measuring the light intensity of the laser light after the beam is passed through the cabin of the vehicle and determining the concentration of ethanol vapor by means of spectral analysis of the dependence of the light intensity on the ethanol concentration.

9. The method according to claim 8, wherein the wavelength of the light source is tuned over a wavelength range including a part of, or a whole of, an absorption 'plateau' located in proximity of the sharp absorption feature of ethanol.

10. The method according to claim 9, wherein before the sending of the laser light beam through the cabin of the vehicle, a background signal, which contains an absorption signal from atmospheric gases and characteristics of the light source including any distortion of a received optical signal, is recorded and removed from the measuring and determining.

11. The method according to claim 10, wherein the method further comprises generating a second light beam from a second light source with a wavelength corresponding to an absorption feature of a tracer gas selected from the group consisting of carbon dioxide and water vapor, sending the generated second light beam from the second light source through the cabin of the vehicle containing a sample of exhaled air, measuring the light intensity of the light from the second light source and determining the level of carbon dioxide or water vapor in the cabin of the vehicle based on the measuring of the light intensity of the light from the second source, and then determining a level of alcohol in the breath using the determined concentration of the ethanol vapor and the determined tracer gas level in the cabin.

12. The method according to claim 9, wherein the wavelength is also tuned over a wavelength range covering a single absorption line or multiple absorption lines of a tracer gas selected from the group consisting of carbon dioxide and water vapor.

13. A method for detecting the presence of ethanol vapor in air from an exhaled breath of a human, comprising
    generating from a laser light source a modulated beam of laser light at a wavelength corresponding to an absorption feature of ethanol within the wavelength range of 3.28-3.52 μm, or within one or more of the wavelength ranges of 6.49-7.46 μm, 7.74-8.33 μm, 8.84-10.10 μm, 10.7-12.00 μm,
    passing the modulated beam of laser light outside of a device in which the laser light source is housed and through a space, outside and separate from the device, containing the exhaled breath, and
    measuring the light passing through the space using the Wavelength Modulation Spectroscopy (WMS) method, and determining a level of ethanol vapor in the exhaled breath based on the light detected after the beam is passed through the space.

14. The method according to claim 13, wherein the method further comprises generating a source of light of a wavelength corresponding to an absorption spectrum of a tracer gas selected from the group consisting of carbon dioxide and water vapor, present in the exhaled air, and sending the source of light through the space containing the exhaled breath, measuring an intensity of the light passing through the space and determining the level of tracer gas in the exhaled breath based on the measured intensity of the light, and then determining the level of ethanol vapor in the exhaled breath by means of the determined level of ethanol vapor and the determined level of tracer gas in said space.

15. A system for remote detection of ethanol vapor concentration in exhaled air, comprising a laser light source in a housing, and a detector for detecting the intensity of laser light from the laser light source emitting at a wavelength corresponding to the spectrum of ethanol absorption, wherein the which the laser light source is contained and across a measurement space outside and separate from the housing, wherein the system is equipped with a synchronizing-calculating module for determination of the concentration of ethanol by means of spectral analysis which is connected to the detector for detecting the light intensity, and wherein the laser light source emits a beam of laser light in the wavelength range of 3.28-3.52 μm, or within one or more of the wavelength ranges of 6.49-7.46 μm, 7.74-8.33 μm, 8.84-10.10 μm, 10.7-12.00 μm.

16. The system according to claim 15, wherein the light source is a tunable, single-mode semiconductor laser of GaInAsSb/AlGaInAsSb.

17. The system according to claim 15, wherein the light source is a tunable quantum cascade laser.

18. The system according to claim 17, wherein the light source is an Interband Cascade Laser (ICL).

19. The system according to claim 15, wherein the light source is a tunable vertical-cavity surface-emitting laser (VCSEL).

20. The system according to claim 15, wherein the light beam is created by difference frequency generation (DFG), which generates light by means of differential mixing of light waves from two lasers.

21. The system according to claim 15, wherein the light source is configured to emit a light beam with a wavelength of 3.345 μm or 7.174 μm or 8.057 μm or 9.377 μm or 11.372 μm, and optionally further wavelength tuned through a sharp absorption feature of ethanol vapor, which occur at wavelengths of 3.345 μm or 7.174 μm or 8.057 μm or 9.377 μm or 11.372 μm.

22. The system according to claim 15, wherein the light source is additionally tuned over a wavelength range covering a single absorption line or multiple absorption lines of a tracer gas selected from the group consisting of carbon dioxide and water vapor, in order to determine the absolute concentration of ethanol in the exhaled air.

23. The system according to claim 15, wherein the system is equipped with an additional source of laser light at a wavelength corresponding to an absorption line of tracer gas, selected from the group consisting of carbon dioxide and water vapor, contained in the exhaled breath, in order to determine the absolute concentration of ethanol in the exhaled air.

24. The system according to claim 15, wherein the system is configured to detect the presence of alcohol vapor in the passenger compartment of a vehicle, using a beam of light with a wavelength of 3.345 μm.

25. The system according to claim 15, wherein the laser light source and the detector are located on opposite sides of the measurement space.

26. The system according to claim 15, wherein the system is equipped with a retro-reflector to redirect the beam to the detector, where the laser light source and the detector are on a same side of the measurement space and the retro-reflector is located on an opposite side of the measurement space.

* * * * *